United States Patent [19]

Pestellini et al.

[11] 4,188,323

[45] Feb. 12, 1980

[54] DERIVATIVES OF 2-OXAZOLYDONE AND METHODS FOR PREPARING THE SAME

[75] Inventors: Vittorio Pestellini; Mario Ghelardoni; Claudio Bianchini; Piero Del Soldato; Giovanna Volterra; Alberto Meli, all of Florence, Italy

[73] Assignee: A. Menarini S.A.S., Italy

[21] Appl. No.: 905,047

[22] Filed: May 11, 1978

[30] Foreign Application Priority Data

Sep. 22, 1977 [IT] Italy .................................. 9578 A/77

[51] Int. Cl.² .................... C07D 263/24; A61K 31/42
[52] U.S. Cl. .................................. 548/229; 424/272; 548/232
[58] Field of Search ...................... 260/307 C; 424/272

[56] References Cited

U.S. PATENT DOCUMENTS

| | | | |
|---|---|---|---|
| 3,062,826 | 11/1962 | Lunsford | 260/307 C |
| 3,062,828 | 11/1962 | Lunsford | 260/307 C |
| 3,331,850 | 7/1967 | Youngsdale | 260/307 C |
| 3,455,946 | 7/1969 | Wilhelm et al. | 260/307 C |
| 3,541,130 | 11/1970 | Koppe et al. | 260/307 C |
| 3,542,872 | 11/1970 | Koppe et al. | 260/307 C |
| 3,654,298 | 4/1972 | Douzon et al. | 260/307 C |
| 3,742,023 | 6/1973 | Koppe et al. | 260/307 C |

*Primary Examiner*—Mary C. Lee
*Attorney, Agent, or Firm*—McGlew and Tuttle

[57] ABSTRACT

A compound having pharmacological properties comprising the structural formula

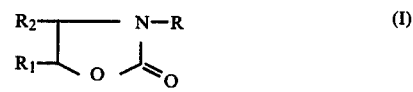

wherein R is selected from the isopropyl, n-octyl, n-butyl or isobutyl groups; $R_1$ is selected from the 1-naphthyloxymethyl, (2-allylphenoxy)-methyl, 4-nitrophenyl, {2-[(tetrahydrofurfuryl)oxy-]-phenoxy}-methyl, [4-(2-methoxyethyl)phenoxy]methyl, 4-isopropylthiophenyl, 4-acetaminophenoxymethyl groups; and $R_2$ represents a hydrogen atom or a methyl group. A method for synthetizing the compound is also disclosed comprising the cyclization of aminoalcohol or halogenurethane.

6 Claims, No Drawings

DERIVATIVES OF 2-OXAZOLYDONE AND METHODS FOR PREPARING THE SAME

BACKGROUND OF THE INVENTION

The present invention relates in general to compounds with pharmacological properties particularly B-adrenolytic or vasodilator properties.

SUMMARY OF THE INVENTION

The present invention comprises derivatives of 2-oxazolydone and methods for making them. These compounds have been found to have interesting pharmacological properties, such as B-adrenolytic or vasodilator properties and in particular to have a long acting action. A disadvantage which exists with the use of many drugs is that they have a pharmacologically valuable action for only a short time, so that repeated daily administrations of the drug are required. In order to obtain drugs which have an action that lasts long enough so that it is possible to reduce the frequency of dosing, thus providing a more uniform therapeutic effect, compounds have been synthetized according to the invention, corresponding to the following general structure formula (I):

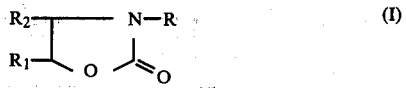

wherein R is selected from the isopropyl, n-octyl, n-butyl or isobutyl groups; $R_1$ is selected from the 1-naphthyloxymethyl, (2-allylphenoxy)-methyl, 4-nitrophenyl, {2-[(tetrahydrofurfuryl)oxy-]-phenoxy}-methyl, [4-(2-methoxyethyl)phenoxy]methyl, 4-isopropylthiophenyl, 4-acetaminophenoxymethyl groups; and $R_2$ represents a hydrogen atom or a methyl group.

Accordingly, an object of the present invention is to provide a compound with the aforementioned formula.

A further object of the present invention is to provide a method for forming the aforementioned compound.

A still further object of the present invention is to provide a method for using the aforementioned compound to utilize its pharmacological properties.

The various features of novelty which characterize the invention are pointed out with particularity in the claims annexed to and forming a part of this disclosure. For a better understanding of the invention, reference should be made to the accompanying descriptive matter in which there is illustrated a preferred embodiment of the invention.

DESCRIPTION OF THE PREFERRED EMBODIMENT

Compounds that are among the above disclosed general structure and which are examples of the present invention are:

(1) 3-isopropyl-5-(1-naphtyloxymethyl)-2-oxazolydone
(Formula I: $R=CH(CH_3)_2$;

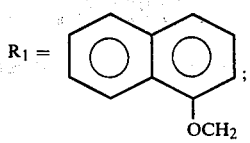

and $R_2=H$)
m.p.=117°–19° C. (acetone/H2O)
I.R. (Nujol), $\gamma$ max (cm$^{-1}$): 1730 (CO)
H-NMR (CDCl$_3$), $\delta$ (p.p.m.): 1.25 (d, 2×CH$_3$) 3.6–3.8 (m, CH$_2$) 4.1–4.5 (m, CH$_2$+CH) 4.8–5.2 (m, CH) 6.9–8.3 (m, C$_{10}$H$_7$).

(2) 3-isopropyl-5-(4-acetaminophenoxymethyl)-2-oxazolydone
(Formula I: $R=CH(CH_3)_2$;

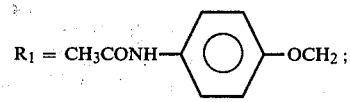

$R_2=H$).
m.p.=152°–55° C.
I.R. (Nujol), $\gamma$ max (cm$^{-1}$): 3240 (NH) 1725 (CO)
H-NMR (DMSO), $\delta$ (p.p.m.): 1.15 (d, 2×CH$_3$) 2.0 (s, CH$_3$) 3.3–3.45 (m, CH$_2$), 3.45–3.8 (m, CH) 4.0 (enlarged d, CH$_2$) 4.6–4.9 (m, CH) 6.8–7.6 (m, C$_6$H$_4$) 9.8 (s, NH).

(3) 3-isopropyl-5-(2-allylphenoxymethyl)-2-oxazolydone (Formula I: $R=CH(CH_3)_2$;

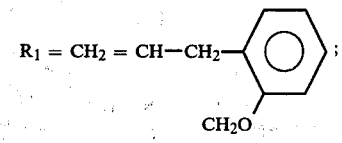

$R_2=H$).
m.p. 50°–2° C.
I.R. (Nujol), $\gamma$ max (cm$^{-1}$): 1730 (CO)
H-NMR (CDCl$_3$), $\delta$ (p.p.m.): 1.2 (d, 2×CH$_3$) 3.2–3.6 (m, CH$_2$+CH) 3.8–4.2 (m, 2×CH$_2$) 4.5–5.1 (m, CH+CH$_2$), 5.3–6.0 (m, CH) 6.6–7.1 (m, C$_6$H$_4$).

(4) 3-isobutyl-5-{2[(tetrahydrofurfuryl)oxy]phenoxy}-methyl-2-oxazolydone
(Formula I: $R=C(CH_3)_3$;

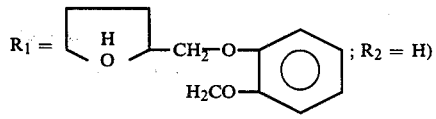

m.p. 104°–106° C.
I.R. (Nujol), $\gamma$ max (cm$^{-1}$): 1720 (CO)
H-NMR (CDCl$_3$), $\delta$ (p.p.m.): 1.5 (s, 3×CH$_3$) 1.9–2.3 (m, 2×CH$_2$) 3.7–4.6 (m, 4×CH$_2$+2×CH) 7.1–7.3 (m, C$_6$H$_4$).

(5) 3-isopropyl-5[4(2-methoxyethyl)phenoxy]methyl-2-oxazolydone
(Formula I: $R=CH(CH_3)_2$;

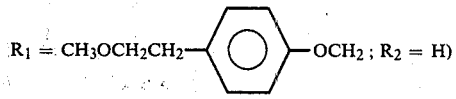

m.p. 78.5°–79.5° C.
I.R. (Nujol), $\gamma$ max (cm$^{-1}$): 1720 (CO)
H-NMR (CDCl$_3$), $\delta$ (p.p.m.): 1.25 (d, 2×CH$_3$) 2.9 (t, CH$_2$) 3.4 (s, CH$_3$) 3.4–3.9 (m, 2×CH$_2$+CH) 4.1 (d enlarged, CH$_2$) 4.6–4.9 (m, CH) 6.8–7.3 (m, C$_6$H$_4$).

(6) 3-n-octyl-4-methyl-5(4-isopropylthiophenyl)-2-oxazolydone (Formula I: R=n—$C_8H_{17}$;

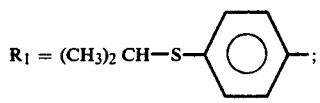

$R_2=CH_3$)

m.p. 48°-50° C.

I.R. (Nujol), γ max ($cm^{-1}$): 1735 (CO)

H-NMR (DMSO), δ (p.p.m.): 0.8 (t, $CH_3$) 0.9-1.6 (m, 3×$CH_3$+6×$CH_2$) 2.8-3.4 (m, $CH_2$+CH) 4.0-4.4 (m, CH) 5.6 (d, CH) 7.1-7.5 (m, $C_6H_4$).

(7) 3-isopropyl-5(4-nitrophenyl)-2-oxazolydone (Formula I: R=CH($CH_3$)$_2$;

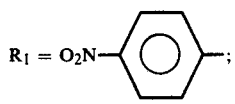

$R_2$=H)

m.p. 84.5°-85.5° C.

I.R. (Nujol), γ ($cm^{-1}$): 1725 (CO)

H-NMR (CDCl$_3$), δ (p.p.m.): 1.2 (d, 2×$CH_3$) 3.4-3.6 (m, CH) 4.0-4.4 (m, $CH_2$) 5.7 (t, CH) 7.6-8.3 (m, $C_6H_4$).

The present invention also comprises corresponding synthesis processes for the production of compounds in the general formula I. As non-limiting examples the following synthesis methods are disclosed:

(a) Formation by the cyclization of aminoalcohol having the general formula (II):

wherein R, $R_1$ and $R_2$ represent the above mentioned atoms or groups, respectively for formula I with carbonyl chloride in an appropriate solvent such as for example dioxane in a basic medium.

(b) Formation by cyclization with alkaline hydrate of halogenurethane having the general formula (III):

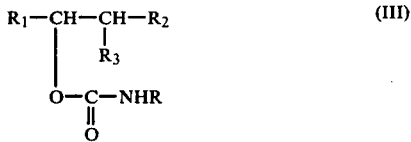

wherein R, $R_1$ and $R_2$ represent the above mentioned atoms or groups respectively for formula I and $R_3$ is a halogen atom, obtained by treatment with the appropriate isocyanate from the suitable halogenated alcohol.

EXAMPLE I 0.11 mole of a 20% carbonyl chloride solution in toluene are added slowly to 0.1 mole of aminoalcohol having the general formula (II) in 100 ml of a suitable solvent such as dioxane and 10 ml of triethylamine. After maintaining the mixture some hours under stirring at room temperature, the mixture is filtered and concentrated. The residue obtained is crystallized from the appropriate solvent.

EXAMPLE II 0.1 mole of halogenurethane having the general formula (III) are kept under reflux in 100 ml of a suitable solvent such as ethanol, or water, containing 0.11 mole of alkaline hydrate. The solvent is removed under vacuum; the product obtained is crystallized from the appropriate solvent.

The products corresponding to general formula (I) have a pharmacological activity and can be used in therapy, in particular as B-adrenolytic with long acting activity. Such activity has been evaluated by determining the capacity for inhibiting tachycardia induced by isoprenalyne in anaesthetized rat. The evaluation of the inventive products (compounds 1 through 5 above) in respect to a comparison product (propanolol) has been carried out taking into account the areas under the time-response curve, with relation to the percentage of animals that feel the effects of the drug at different times (potency ratio; Table I).

TABLE I

| PRODUCT | POTENCY RATIO |
| --- | --- |
| 1 | 8.5 |
| 2 | 5 |
| 3 | 5 |
| 4 | 8.5 |
| 5 | 1.5 |
| propanolol | 1 |

The compounds, dissolved in dimethylsulphoxide, have been administered in the doses of 10 mg/Kg per os; isoprenalyne (0.12 mg/Kg) has been administered by intravenous injection.

Compound 6 showed a vasodilator action at cerebral level (test of protective action against anoxemia caused by cerebral asphyxia according to the technique of I. Rosmer, J. Legros and C. Berger, Arch. Int. Pharmacodyn. 194, 375-380, 1971). This action has been found to still be intense even many hours after administration of the product.

LD 50 (os) of products 1-7 resulted to be greater than 1500 mg/Kg. in mice.

While specific embodiments of the invention have been shown and described in detail to illustrate the application of the principles of the invention, it will be understood that the invention may be embodied otherwise without departing from such principles.

What is claimed is:

1. A member selected from the group consisting of 3-isopropyl-5-(1-naphthyloxymethyl)-2-oxazolydone; 3-isopropyl-5-(4-acetaminophenoxymethyl)-2-oxazolydone; 3-isobutyl-5-{2[(tetrahydrofurfuryl)oxy]phenoxy}methyl-2-oxazolydone; 3-n-octyl-4-methyl-5-(4-isopropylthiophenyl)-2-oxazolydone; 3-isopropyl-5-(4-nitrophenyl)-2-oxazolydone.

2. 3-isopropyl-5-(-1-naphthyloxymethyl)-2-oxazolydone.

3. 3-isopropyl-5-(4-acetaminophenoxymethyl)-2-oxazolydone.

4. 3-isobutyl-5-{2[(tetrahydrofurfuryl)]oxy phenoxy}methyl-2-oxazolydone.

5. 3-n-octyl-4-methyl-5-(4-isopropylthiophenyl)-2-oxazolydone.

6. 3-isopropyl-5-(4-nitrophenyl)-2-oxazolydone.

* * * * *